United States Patent [19]

Jousson

[11] Patent Number: 4,830,032
[45] Date of Patent: May 16, 1989

[54] POWER DRIVEN FLOSSING DEVICE

[75] Inventor: Pierre-Jean Jousson, Geneva, Switzerland

[73] Assignee: Les Produits Associes LPA-Broxo S.A., Switzerland

[21] Appl. No.: 937,569

[22] Filed: Dec. 3, 1986

[51] Int. Cl.⁴ .............................................. A61C 15/00
[52] U.S. Cl. ........................................................ 132/323
[58] Field of Search .................. 132/92, 89, 91, 92 R, 132/322, 323, 324, 325, 326, 327

[56] References Cited

U.S. PATENT DOCUMENTS

| | | | |
|---|---|---|---|
| 413,001 | 10/1889 | Walsh | 132/91 |
| 1,479,364 | 1/1924 | Browne | 132/92 R |
| 1,644,390 | 10/1927 | Miller | 132/91 |
| 3,421,524 | 1/1969 | Waters | 132/92 R |
| 3,897,796 | 8/1975 | Erickson | 132/89 |
| 4,162,687 | 7/1979 | Lorch | 132/91 |
| 4,206,774 | 6/1980 | Griparis | 132/92 R |
| 4,235,253 | 11/1980 | Moore | 132/92 R |
| 4,265,257 | 5/1981 | Salyer | 132/92 R |
| 4,307,740 | 12/1981 | Florindez et al. | 132/92 R |

*Primary Examiner*—John J. Wilson
*Attorney, Agent, or Firm*—Kane, Dalsimer, Sullivan, Kurucz, Levy, Eisele and Richard

[57] ABSTRACT

An automatic toothbrush wherein the brush can be replaced by a floss holder driven by the toothbrush motor.

7 Claims, 3 Drawing Sheets

POWER DRIVEN FLOSSING DEVICE

FIELD OF THE INVENTION

This invention relates generally to an oral hygiene system and more specifically, the invention relates to a power-driven floss holder.

BACKGROUND OF THE INVENTION

As is well known, plaque is a primary cause of dental ulcerations and disintegrations of the supporting bone structure of the teeth, and of periodontal diseases. There are many prophylactic dental products which have been proposed for removing the mucous plaque found in the interproximal spaces, and on the proximal surfaces of the teeth. The most commonly used preventative dentistry product is the toothbrush, and more recently, power driven tooth brush. A problem arises with such toothbrushes in that they do not sometimes reach into the interproximal spaces, and the proximal surfaces of the teeth, thereby failing to remove the mucous plaque as well as other foreign matter.

Flossing has proven effective and may also be recommended for cleaning between teeth while at the same time stimulate the gums. However, normal manipulation of dental floss has its limitations depending on the dexterity of the individual. Normally the number of movements of the floss is reduced and in the neighborhood of 15-20 movements per minute.

PATENT INFORMATION DISCLOSURE STATEMENT

U.S. Pat. No. 4,235,253 describes a dental floss device driven by a motor via a motion transformer such that the floss moves in a vertical direction up and down. U.S. Pat. No. 3,421,524 described an attachment for an electric toothbrush which provides orbital movement of dental floss in the end of a tip. U.S. Pat. No. 4,265,257 describes a dental floss device driven by a vibrating source and completed by an elongated non-vibratory arm mounted upon the vibratory source for extending the dental floss.

U.S. Pat. No. 4,307,740 shows the provision of an oscillating arm with a cam slot and a pin extending into the slot so as to produce a complicated motion. By means of this arrangement the dental floss moves on the interdental surface of the teeth in an up and down direction, and simultaneously in sideward direction back and forth in contact with the inter-dental surfaces of the teeth. U.S. Pat. No. 4,338,957 describes a device having an oscillating driving shaft fixed to a sleeve which imparts oscillating motion to a support. In this manner a floss segment reciprocates between tines provided in the device with a non-elastic loop of dental floss being supported on an oscillating support while an elastic part or loop of the floss is supported on a stationary support. With respect to the dental floss of the present invention, mention can be made of U.S. Pat. No. 3,897,796 wherein the colored portions of the dental floss are the waxed portions, and the colors thereof serves only to mark these waxed portions, so that the user can distinguish them from the waxed uncolored portions. It is not the patentee's intention that the color should disappear when a little floss is used because the cleaning friction is effected with the unwaxed, uncolored portions. Furthermore, the markings in the patentee's floss are not obliterated by its use and the coloring does not come off in the salival environment of the mouth. British Pat. No. 2,024,630 is of interest for its showing of a tooth cleaner or dental floss consisting of a carrier thread, which is tufted at intervals with small bristles, the bristles being provided with a dentifrice and/or a disinfecting agent. British Pat. No. 2,128,133 discloses a dental tape for use in the removal of plaque from teeth wherein the tape is constituted by a length of incipiently fibrillatable plastics film. This is a film which fibrillates spontaneously on rubbing against the surface of a tooth and thereby indicating that it is worn and must be pulled away. The tape may be colored by including a pigment in the plastic mass from which the tape is made. As a result, the complete mass of the tape is colored and this color cannot disappear when the tape is used.

As will be seen hereinafter, none of these patents disclose, hint or suggest in any manner whatsoever the applicant's novel unique and unobvious dental flossing apparatus.

OBJECTS AND SUMMARY OF THE INVENTION

The principal object of the invention is to provide a power-driven flossing device for giving optimum motion to the dental floss to clean between teeth without cutting the gums.

Another object of the invention is to provide a novel dental floss covered by colored wax along its entire length so as to indicate parts thereof which have been used by the disappearance of the colored wax.

These objects are achieved in accordance with the invention by means of an automatic toothbrush having a power handle and to which may be removably secured a dental floss holder for imparting to a dental floss a partly hyperboloidal revolution. It is contemplated that the number of movements of the floss will be high and as much as 3600 movements per minute. In a preferred embodiment of the invention, the dental floss can be of novel design and be entirely coated with a removable colored wax coating to indicate the portions thereof already used.

DESCRIPTION OF THE PREFERRED EMBODIMENTS

Figure 1:
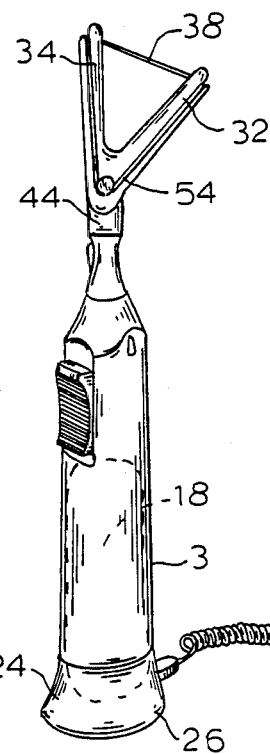
FIG. 1 is a perspective view showing the electric toothbrush power handle with dental floss holder of the invention.
Figure 1:
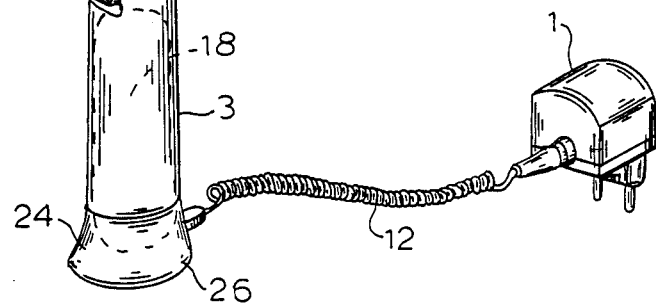

Referring descriptively to the drawing:

An exemplary apparatus usable with the invention comprises a plug-in transformer 1 which provides safe extras-low voltage which can range from 120 volts to 240 volts at a rated frequency of 50 to 60 Hz with preferably an input power of 6 Watts and a secondary voltage ranging from 14 volts per 60 Hz to 14 volts per 50 Hz. The transformer has an output power of 3 Watts and is designed for continuous operation in idle running. The transformer shown is connected to electric toothbrush 3 and specifically the drive motor therein by a coiled cord 12. Switch (19) for varying the output speed of the shaft (52) which is adapted to rotate recipient as a result of the oscillation of the motor 18. Thus the motor has an oscillating armature and a permanent magnet. It should be understood that any automatic toothbrush is usable with this invention including electric, battery as well as rechargeable battery powered.

Figure 4:
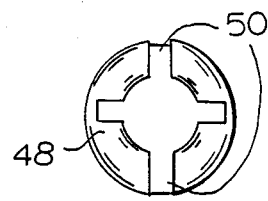
FIG. 4 is a cross-sectional view, taken along line 66 of FIG. 2 and showing the outer end of the connection uniting the floss holder to the power shaft.
Figure 2:
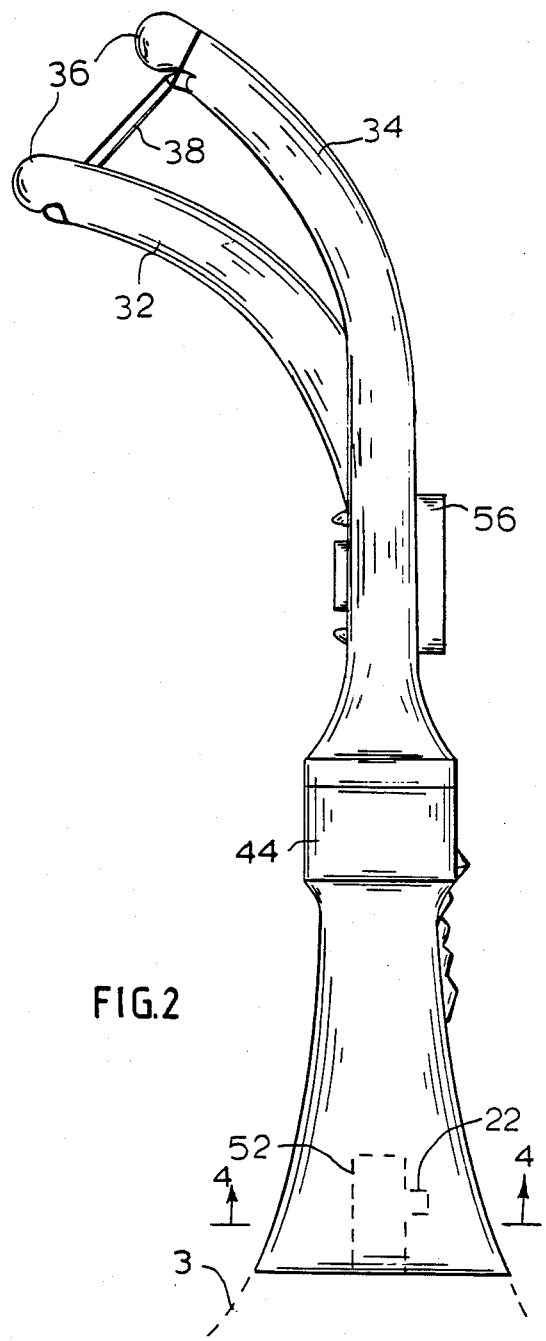
FIG. 2 is an elevational view with certain parts broken away of the dental floss holder.
Figure 3:
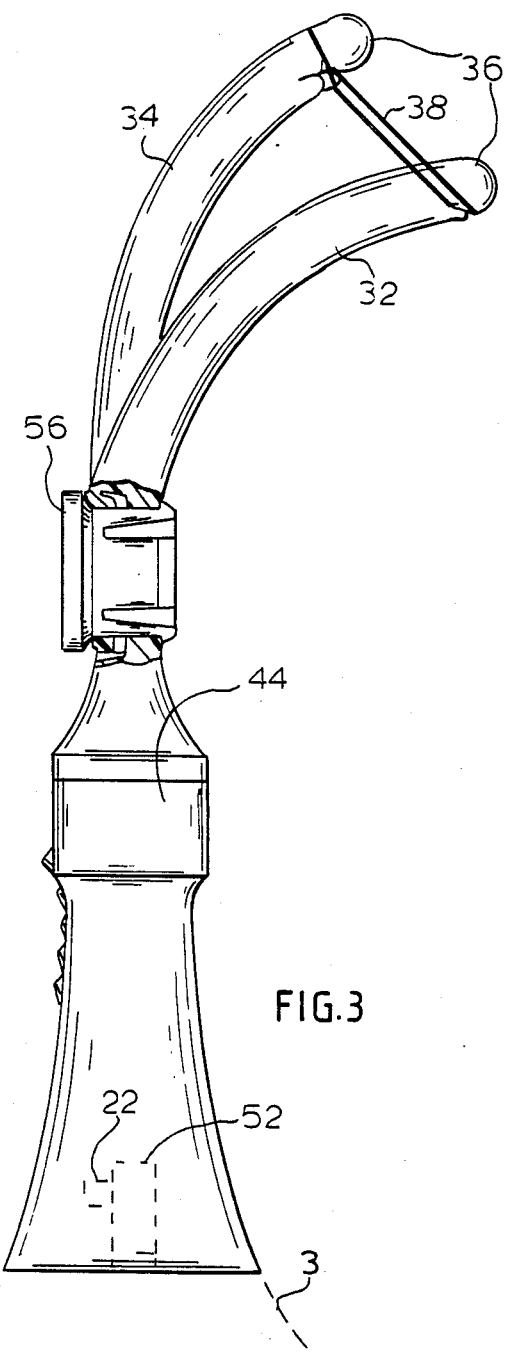
FIG. 3 is a similar view, partly in section of the active part of the floss holder.

A dental floss holder (30) in accordance with the invention comprises a pair of downwardly curved tines (32 and 34) with tine (34) being smaller than tine (32). The proximal end of each tine has a rounded surface (36) around which dental floss (38) is wound for use. The longer tine (32) is bent at a much greater angle than smaller tine (34). The lower end of base 44 as shown in FIG. 4 has a substantially cruciform inner arrangement of compartments with slot (50) being open so as to facilitate introduction therein of pin (22) of shaft (52). It will be understood that the floss holder is molded from a very rigid plastic material such as polycarbonate, polyethylene or polystyrene resin in order to avoid that during use the fork or tines holding the dental floss bends and allows the floss to get out from its guiding channels (54). On the top surface of the floss holder is provided a button (56) which is spaced slightly from the upper surface of the floss holder to permit tightening of the loop of floss therearound.

Figure 5:
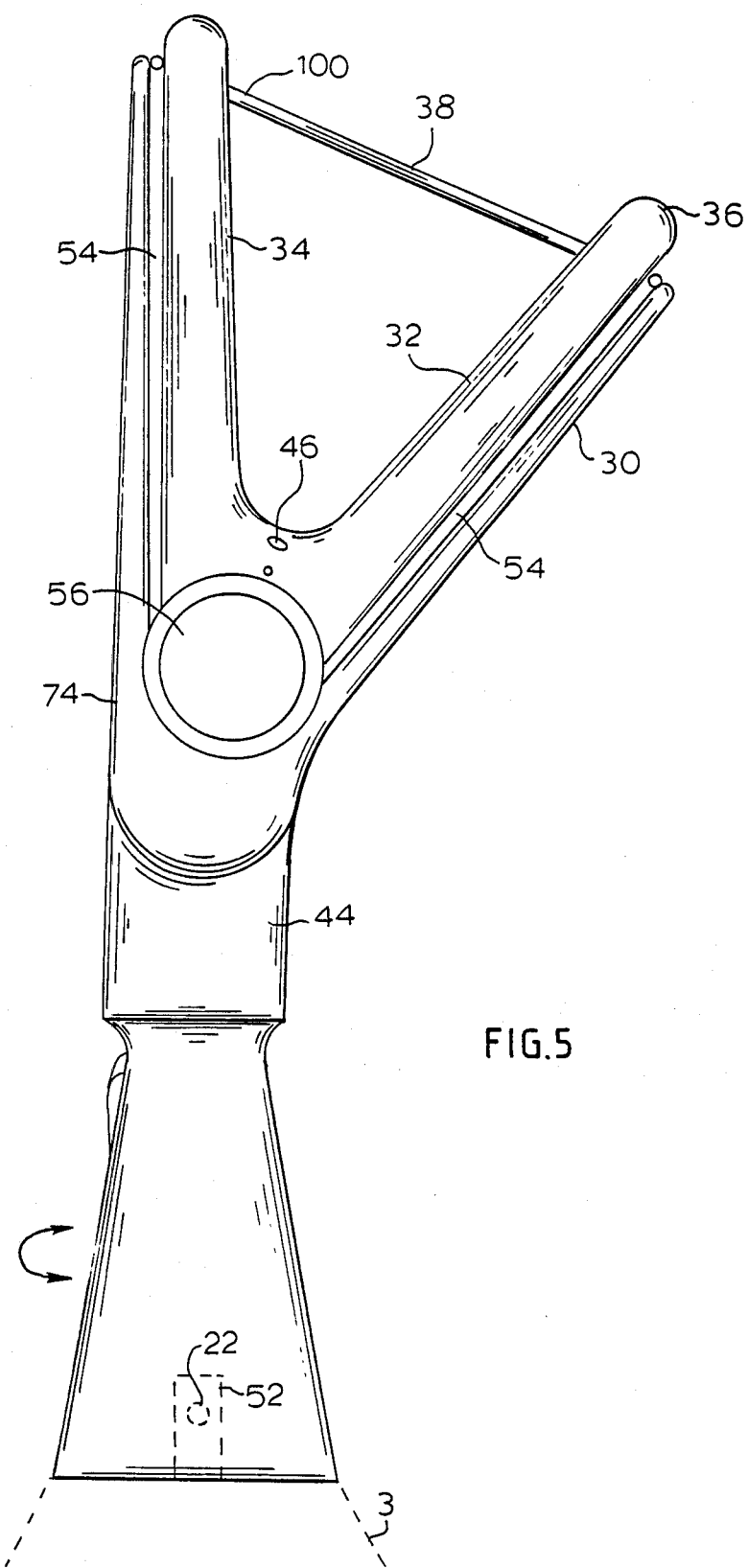
FIG. 5 is a top plan view of the floss holder shown in enlarged detail.

In order to obtain an effective cleaning action on the part of the floss and without irritating or cutting the gum, the dental floss holder must be shaped and disposed as drawn in order to have the floss (38) describe in the space between the tines (32 and 34) a portion of hyperboloidal revolution. In the embodiment shown the lower end of the floss base 44 is friction fitted on the end of shaft (52). As shown by arrow in FIG. 5 a rotational oscillating motion is imparted to the floss holder 30. This motion has a frequency which will range between 40 to 60 c/s. The motion of the dental floss holder must be very small and preferably only about one to two mm at the dental floss level, which means a very small angle of oscillation of the motor shaft of only a few degrees. Departing from the prior art, the floss of the present invention can have thereon a coating of wax which disappears when the floss is used to make clearly apparent the portions of the floss already used. This is achieved by placing a coating of wax to which has been added a coloring pigment which rubs off when using the floss. This coating is shown in FIG. 5 and is referenced 100. The pigment may be incorporated in the wax in any manner known per se. The color coding, such as a blue wax coating, makes it apparent to the user which portions of the floss have been used, so that he will not reuse these portions. This therefore, minimizes passage of harmful bacteria from one interdental space to another space.

While the principles of the invention have been described above in connection with preferred specific apparatus and applications, it is to be understood that the description is made only by way of example, and does not limit the scope of the invention, except as set forth in the appended claims.

What is claimed is:

1. An oral hygiene apparatus comprising in combination:
   a handle having a top end and a bottom end, a motor housed in said handle, and having a shaft protruding therefrom, said shaft having a longitudinal axis and being imparted a rotational oscillating motion by said motor;
   a dental floss holder having a base on one end fitting on said shaft and another end divided into a pair of forks of unequal length, including a smaller fork and a longer fork, thereby holding a length of floss at a skew line with respect to said longitudinal axis of said shaft.

2. The invention in accordance with claim 1 wherein said forks have extremities bent along different axes and having floss stretched therebetween.

3. The invention in accordance with claim 2 wherein said base is integral with said forks and terminates at the end opposite said forks into a connector adapted to frictionally and removably fit on such shaft and to impart a portion of a hyperboloid revolution to said forks.

4. The invention in accordance with claim 3 wherein means are on said base for tightening said floss between said forks.

5. The apparatus according to claim 3 wherein said floss has a coating of colored wax.

6. The apparatus according to claim 1, wherein said base includes a connector removably securable to said shaft and lying within the axis of the smaller fork.

7. The apparatus according to claim 1, wherein the outer ends of said forks have rounded extremities and grooves between said rounded extremities and the rest of said fork for receiving said dental floss.

* * * * *